(12) United States Patent
Yamada et al.

(10) Patent No.: US 8,223,332 B2
(45) Date of Patent: Jul. 17, 2012

(54) MERCURY MEASURING APPARATUS FOR MEASURING MERCURY CONTAINED IN SAMPLE COMPOSED MAINLY OF HYDROCARBON

(75) Inventors: Yasuyuki Yamada, Takatsuki (JP); Munehiro Hoshino, Takatsuki (JP)

(73) Assignee: Nippon Instruments Corporation, Tokyo (JP)

( * ) Notice: Subject to any disclaimer, the term of this patent is extended or adjusted under 35 U.S.C. 154(b) by 353 days.

(21) Appl. No.: 12/674,354

(22) PCT Filed: Aug. 19, 2008

(86) PCT No.: PCT/JP2008/002229
§ 371 (c)(1),
(2), (4) Date: Feb. 19, 2010

(87) PCT Pub. No.: WO2009/028149
PCT Pub. Date: Mar. 5, 2009

(65) Prior Publication Data
US 2011/0299072 A1 Dec. 8, 2011

(30) Foreign Application Priority Data
Aug. 27, 2007 (JP) .................. 2007-220138

(51) Int. Cl.
*G01J 3/42* (2006.01)
*G01N 25/00* (2006.01)
*G01N 37/00* (2006.01)
(52) U.S. Cl. ..... 356/319; 73/23.39; 73/23.37; 73/23.41; 73/23.2
(58) Field of Classification Search .......... 356/319; 73/61.52, 23.39, 23.37, 23.2, 23.41; 436/81, 436/76, 50
See application file for complete search history.

(56) References Cited

U.S. PATENT DOCUMENTS

| 4,758,519 A | 7/1988 | Nakao et al. |
| 5,098,658 A * | 3/1992 | Huber .......................... 422/78 |
| 6,475,802 B2 * | 11/2002 | Schaedlich et al. ........... 436/81 |
| 7,552,617 B2 * | 6/2009 | Danilchik .................... 73/23.41 |
| 2004/0031313 A1 | 2/2004 | Tanida et al. |
| 2004/0237634 A1 | 12/2004 | Makino et al. |

FOREIGN PATENT DOCUMENTS

| EP | 0 172 521 A2 | 2/1986 |
| JP | 62-5641 Y2 | 2/1987 |
| JP | 1-54655 B2 | 11/1989 |
| JP | 2001-221787 A | 8/2001 |
| JP | 2004-093484 A | 3/2004 |
| JP | 2004-354067 A | 12/2004 |

OTHER PUBLICATIONS

English translation of International Preliminary Report on Patentability; Mar. 18, 2010.

* cited by examiner

*Primary Examiner* — Layla Lauchman
(74) *Attorney, Agent, or Firm* — Sughrue Mion, PLLC

(57) ABSTRACT

To provide a mercury measuring apparatus of a closed system capable of performing automatically a process ranging from collection to injection of the sample composed mainly of hydrocarbon, which is effective to accomplish a highly reliable measurement. The mercury measuring apparatus 100 includes a column 1 filled with a first adsorbent 11 and a reducing agent 13, an injecting unit 3 for injecting a sample into the column 1, a first heating unit 12, a second heating unit, a mercury collecting tube 18 filled with a second adsorbent 17, a third heating unit 19, a mercury measuring unit 2, gas flow passages FP1, FP2 and FP4, flow switching valves V1 to V3, V5 and V6 for selecting one of the gas flow passages FP1, FP2 and FP4, and a control unit 4.

6 Claims, 13 Drawing Sheets

Fig. 11

| | | TEMPERATURES HELD BY HEATING UNITS °C | | | |
|---|---|---|---|---|---|
| | | FIRST HEATING UNIT | SECOND HEATING UNIT | HALOGEN HEATING UNIT | THIRD HEATING UNIT |
| S1 | INJECTION OF SAMPLE WITH INJECTING UNIT | 160 | 700 | 180 | 160 |
| S2 | COLLECTION OF MERCURY IN SAMPLE AND SEPARATION OF VOLATILE ORGANIC MATTER | 160 | 700 | 180 | 160 |
| S3 | REDUCTION TO METAL MERCURY AND COLLECTION WITH MERCURY COLLECTING TUBE | 700 | 700 | 180 | 160 |
| SB1 | EXCHANGE OF GAS WITHIN COLUMN OF FIRST ADSORBENT UNIT WITH CLEAN AR. | 160 | 700 | 180 | 160 |
| SB2 | EXCHANGE OF GAS WITHIN COLUMN AND MERCURY COLLECTING TUBE WITH CLEAN AR. | 160 | 700 | 180 | 160 |
| SB3 | EXCHANGE OF GAS WITHIN CELL BYPASS WITH CLEAN AR. | 160 | 700 | 180 | 160 |
| SB4 | EXCHANGE OF GAS WITHIN SAMPLE CELL WITH CLEAN AR. | 160 | 700 | 180 | 160 |
| S4 | ISOLATION OF METAL MERCURY FROM MERCURY COLLECTING TUBE | 160 | 700 | 180 | 700 |
| S5 | MEASUREMENT OF METAL MERCURY ISOLATED FROM MERCURY COLLECTING TUBE | 160 | 700 | 180 | 700 |
| SB5 | EXCHANGE OF GAS WITHIN SAMPLE CELL WITH CLEAN AIR | 160 | 700 | 180 | 700 |
| S6 | COOLING OF MERCURY COLLECTING TUBE | 160 | 700 | 180 | 160 |

MERCURY MEASURING APPARATUS FOR MEASURING MERCURY CONTAINED IN SAMPLE COMPOSED MAINLY OF HYDROCARBON

CROSS REFERENCE TO THE RELATED APPLICATION

This application is based on and claims Convention priority to Japanese patent application No. 2007-220138, filed Aug. 27, 2007, the entire disclosure of which is herein incorporated by reference as a part of this application.

FIELD OF THE INVENTION

The present invention relates to an apparatus for measuring mercury, which is contained in a sample composed mainly of hydrocarbon, which sample may be a petrochemical product such as, for example, naphtha, kerosene, gasoline, heavy oil and LPG (liquefied petroleum gas), according to the atomic absorption spectrometry or the atomic fluorescence spectrometry.

BACKGROUND ART

Most of the commercially available petrochemical products contain mercury and, for example, mercury and metallic material, employed to form tanks mounted on an LPG tanker, form amalgam, which dissolve the metallic material of the tanks into petroleum. Also, it has been well known in the art that a sample composed mainly of hydrocarbons such as, for example, naphtha, contain mercury, particularly dimethylmercury. It is also well known that various components of mercury are responsible for the degradation of the capacity of a catalyst such as paradigm or platinum employed for producing various kinds of petrochemical products from naphtha. For this reason, countermeasures have been considered necessary to measure the amount of mercury contained in the sample composed mainly of hydrocarbon and to remove the mercury when the amount of mercury contained in the sample composed mainly of the hydrocarbon exceeds a predetermined value.

Hitherto, attempts for mercury measurement have been made to use a heat-vaporization analyzing apparatus including a sample boat in which a sample composed mainly of hydrocarbon is directly injected. With this heat-vaporization analyzing apparatus, mercury contained in the sample is measured after having been vaporized by heating the sample boat within a combustion tube. Also, during the measurement, additives are added together with the sample to remove interfering gases that are generated from the sample and are likely to disturb the mercury measurement.

However, with the conventional method of measuring mercury discussed above, it has been experienced that when mercury contained in the sample is vaporized by heating, hydrocarbon is simultaneously volatized from the sample to produce an inflammable gas. Accordingly, in order to avoid a rapid generation of the inflammable gas, stringent measurement conditions are required as to the quantity, type and flow rate of the sample and also as to the temperature rise rate of the sample and so on. Also, similarly stringent requirements are imposed on selection of the additives.

In view of the foregoing, the method of measuring mercury and the apparatus therefor have been suggested, in which the severe measuring conditions are alleviated to facilitate measurement of mercury with no difficulty. (See the Patent Document 1 listed below.) According to this mercury measuring method, in a condition while a gas containing no mercury flows through a column, hydrocarbon is injected into the column to allow mercury, contained in a sample composed mainly of hydrocarbon, to be adsorbed by an adsorbent contained within the column. On the other hand, components such as, for example, hydrocarbon left when the mercury is removed by adsorption are discharged to the outside together with the gas and then removed from the column. The column is subsequently inserted in a mercury measuring apparatus, in which the mercury adsorbed by the adsorbent, is heated to vaporize for measurement. At the time of measurement, since even when the mercury is heated to vaporize, hydrocarbon has already been removed from the column, no inflammable gas is generated. Also, since only the gas flowing through the column, but containing no mercury and the mercury adsorbed by the adsorbent remain within the column and the gas, which would undesirably interfere the mercury measurement, does not exist within the column, no addition of additives is required to remove the interfering gas. For this reason, there is no need to set up the severe measuring conditions such as those hitherto required and measurement of mercury can be accomplished easily.

[Patent Document 1] JP Laid-open Patent Publication No. 2001-221787

DISCLOSURE OF THE INVENTION

It has, however, been found that the prior art mercury measuring method discussed above requires the measurement to be performed after mercury contained in the sample composed mainly of hydrocarbon has been adsorbed in the column and the operator has subsequently inserted such column in the mercury measuring apparatus, an apparatus that can be used to execute this mercury measuring method is incapable of performing continuously a first process step of allowing the column to adsorb mercury and a second process step of measuring the mercury, and an injector used to inject a measuring sample such as, for example, naphtha or kerosene requires a manual operation. Therefore, the procedures are complicated and require a large length of time in accomplishing the intended measurement.

In view of the problems and inconveniences inherent in the mercury measurement hitherto encountered with, the present invention has for its object to provide a mercury measuring apparatus of a closed system, in which a process ranging from collection to injection of the sample composed mainly of hydrocarbon is performed automatically, which is effective to provide stable data of a high reliability, and which is easy to operate and capable to measuring the mercury in a short in a matter of minutes.

To this end, a mercury measuring apparatus according to the present invention is an apparatus for measuring mercury contained in a sample composed mainly of hydrocarbon, which includes a column accommodating therein a first adsorbent for adsorbing mercury and a reducing agent for reducing monovalent and bivalent mercury into a metal mercury, an injector for injecting the sample into the column, a first heating unit for heating the first adsorbent within the column, a second heating unit for heating the reducing agent within the column, a mercury collecting tube filled with a second adsorbent for adsorbing the metal mercury, a third heating unit for heating the mercury collecting tube, and a mercury measuring unit for measuring by introducing the metal mercury, which is isolated from the mercury collecting tube then heated by the third heating unit, into a sample cell.

The mercury measuring apparatus of the present invention discussed above also includes a gas flow path defining one of an injecting and collecting passage for introducing a carrier gas from a gas introducing port so as to flow through the first adsorbent and discharging the carrier gas from a gas discharge port, a reducing and collecting passage for introducing the carrier gas from the gas introducing port so as to flow through the first adsorbent, a reducing agent and a second adsorbent and discharging the carrier gas from the gas discharge port, and a measuring passage for introducing the carrier gas from the gas introducing port so as to flow through the second adsorbent and a sample cell and discharging the carrier gas from the gas discharge port; a flow path switching valve for selecting one of the gas flow passages; and a control unit for controlling the first heating unit, the second heating unit, the third heating unit, the injector, the flow path switching valve and the mercury measuring unit.

With the mercury measuring apparatus according to the present invention, since the apparatus automatically performs a process ranging from collection to measurement of the sample composed mainly of hydrocarbon, there is no need for the operator to insert the column, in which mercury has been adsorbed, into the mercury measuring unit such as required in the prior art disclosed in the Patent Document 1 above. Also, since the apparatus is designed of the closed system, stable data having a high reliability can be obtained and the apparatus can be easily operated to accomplish the intended measurement in a matter of minutes.

The mercury measuring apparatus of the present invention is preferably of a type, in which the control unit executes a sample injecting step of injecting a sample into the injector; a collecting and separating step of collecting mercury, contained in the sample, to the first adsorbent and subsequently separating and discharging a volatile organic matter; a mercury reducing and collecting step of causing the first heating unit to heat and vaporize mercury, collected by the first adsorbent, reducing monovalent and bivalent mercury into metal mercury by causing the second heating unit to heat the reducing agent, and causing the metal mercury to be collected by the mercury collecting tube filled with the second adsorbent; a metal mercury isolating step of causing the third heating unit to heat the mercury collecting tube to isolate the metal mercury from the second adsorbent; and a measuring step of measuring the metal mercury, which has been isolated from the mercury collecting tube, with the mercury measuring unit.

In the mercury measuring apparatus of the present invention, the control unit is preferably of a type capable of executing the metal mercury isolating step and the measuring step simultaneously. Particularly where the content of mercury contained in the sample is high, simultaneous execution of the metal mercury isolating step and the measuring step is effective to lower the measuring sensitivity and, therefore, the sample can be measured with no need to dilute the sample.

In the mercury measuring apparatus of the present invention, the gas flow path preferably includes a first gas introducing port, through which a first carrier gas is introduced, and a second gas introducing port, through which a second carrier gas is introduced, in which case the mercury measuring unit is preferably employed in the form of a mercury atomic fluorescence spectrophotometer. The provision of the first gas introducing port and the second gas introducing port makes it possible for two kinds of gases to be introduced and, therefore, the measurement with high sensitivity can be accomplished with the mercury atomic fluorescence spectrophotometer, which forms the mercury measuring unit employed in the practice of the present invention.

In such case, the first carrier gas is preferably introduced from the first gas introducing port during the sample injecting step, the collecting and separating step and the mercury reducing and collecting step, but the second carrier gas is preferably introduced from the second gas introducing port during the metal mercury isolating step and the measuring step, and the mercury measuring unit is preferably employed in the form of a mercury atomic fluorescence spectrophotometer. When the first gas suitable for sample injection, collection and separation, and also mercury reduction and collection is introduced, mercury and a volatile organic matter, both contained in the hydrocarbon, can be assuredly separated from each other with the mercury collected by the adsorbent and, on the other hand, when the second gas suitable for metal mercury isolation and measurement is introduced, it can be measured by the mercury atomic fluorescence spectrophotometer, which forms the mercury measuring unit, with a high sensitivity.

The mercury measuring apparatus of the present invention may preferably include a sample exchanger for exchanging a plurality of samples, which exchanger is controlled by the control unit. This is particularly advantageous that the plurality of the samples can be automatically measured continuously.

BRIEF DESCRIPTION OF THE DRAWINGS

In any event, the present invention will become more clearly understood from the following description of preferred embodiments thereof, when taken in conjunction with the accompanying drawings. However, the embodiments and the drawings are given only for the purpose of illustration and explanation, and are not to be taken as limiting the scope of the present invention in any way whatsoever, which scope is to be determined by the appended claims. In the accompanying drawings, like reference numerals are used to denote like parts throughout the several views, and:

FIG. 11 illustrates a flow chart showing the sequence of operation of the mercury measuring apparatus according to the second embodiment;

BEST MODE FOR CARRYING OUT THE INVENTION

Figure 1:
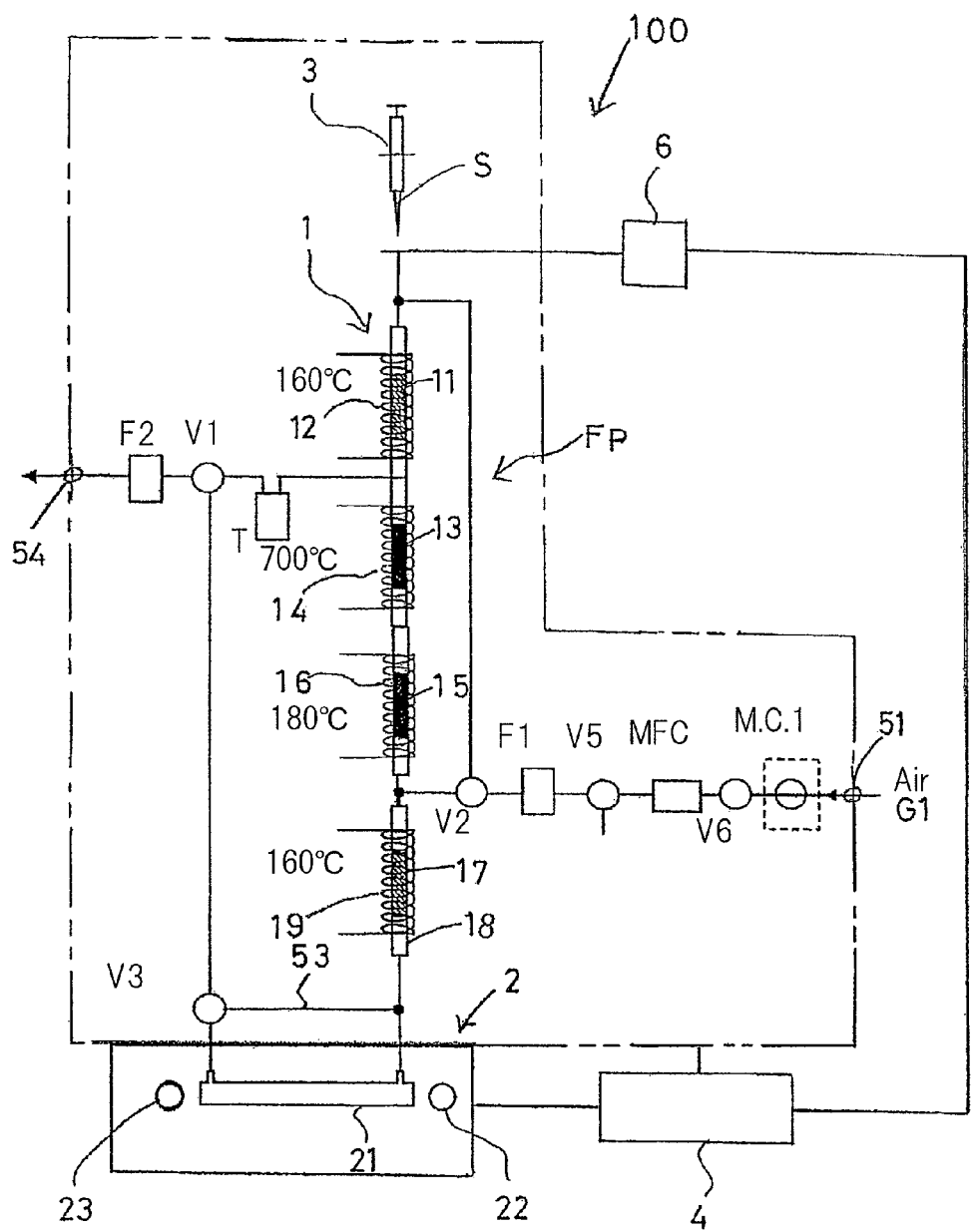
FIG. 1 illustrates a schematic block diagram showing a mercury measuring apparatus according to a first preferred embodiment of the present invention.

Hereinafter, some preferred embodiments of the present invention will be described with reference to the accompanying drawings. FIG. 1 schematically illustrates a mercury measuring apparatus according to the first preferred embodiment of the present invention. It is to be noted that the mercury measuring apparatus 100 has a gas introducing port 51, to which an air G1 to be used as a carrier gas is introduced by and from, for example, an air compressor (not shown) disposed outside the mercury measuring apparatus 100. This mercury measuring apparatus 100 includes a column 1 of an elongated tubular configuration having opposite ends thereof fixed with, for example, silica wool and accommodating therein a first adsorbent 11, a reducing agent 13 for reducing monovalent and bivalent mercury into metal mercury, and an acidic substance removing agent 15 for adsorbing the acidic substance filled therein; a first heating unit 12 for heating the first adsorbent 11 within the column 1; a second heating unit 14 for heating the reducing agent 13 within the column 1; an acidic substance removing agent heating unit 16 for heating the acidic substance removing agent 15 within the column 1; a mercury collecting tube 18 for collecting metal mercury; and an injector such as, for example, a micro syringe for injecting a sample S into the column 1. It is to be noted that in place of the air G1, an oxygen gas may be employed for the carrier gas. It is also to be noted that the column 1 or a column separated from the column 1 may be employed with a sulfur removing agent for removing a sulfur component contained in the sample.

The mercury measuring apparatus 100 referred to above also includes a sample exchanger 6 for exchanging a plurality of samples S; a third heating unit 19 for heating the mercury collecting tube 18 to heat and vaporize metal mercury collected in the mercury collecting tube 18; a mercury measuring unit 2 for introducing metal mercury, isolated from the mercury collecting tube 18 as a result of heating by the third heating unit 19, into a sample cell 21 and measuring such metal mercury; a gas flow path defining one of an injecting and collecting passage FP1, a reducing and collecting passage FP2, a gas exchanging passage FP31 and a measuring passage FP4; flow switching valves V1, V2, V3, V5 and V6 for establishing the gas passages FP1, FP2, FP3 and FP4, respectively; and a control unit 4 in the form of, for example, a computer for controlling the first heating unit 12, the second heating unit 14, the third heating unit 19, the acidic substance removing agent heating unit 16, the injector 3, the flow switching valves V1, V2, V3, V5 and V6, and the mercury measuring unit 2.

The column 1 may be formed either integrally or separately with a column portion, in which the first adsorbent is filled, and a second column portion in which the reducing agent 13 is filled. Depending on the kind of samples and the amount of each samples injected by means of the injector 3, respective temperature, to which the heating units achieve, and respective heating times, during which those heating units are operated, and respective opened or closed lengths of time, during which the various flow switching valves are selectively opened or closed, can be controlled by the control unit 4 and those setting conditions can be stored and used during the subsequent measurements. The injector 3 can be used to inject the sample S either once at a time or repeatedly a number of times. Owning to the repeated injection through the injector 3 a number of times, the intended measurement can be accomplished even though the amount of mercury contained in the sample S is very small. A number of vials each accommodating the sample S such as, for example, naphtha, kerosene or heavy oil diluted with xylene solvent about 10 times are placed on a turntable of the sample exchanger 6.

The mercury measuring unit 2 includes a mercury lamp 22 for emitting an analytical line of 253.7 nm of mercury, an absorption cell 21 capable of passing mercury, which has been collected and isolated from the sample S, therethrough and also capable of transmitting the analytical line therethrough for analysis of the mercury, and a detector 23 for detecting the intensity of the analytical line of the mercury passing through the absorption cell 21 and is employed in the form of a mercury atomic absorption spectrophotometer 2 capable of determining the content of mercury in the sample S through processing of signals fed from the detector 23. Alternatively, the mercury measuring unit 2 may include a mercury lamp for emitting an analytical line of mercury, a flow cell for passing mercury, which has been collected and isolated from the sample S, therethrough, and a detector for detecting fluorescence of mercury generated from the sample S within the flow cell that has been radiated with the analytical line from the mercury lamp and may be employed in the form of a mercury atomic fluorescence spectrophotometer capable of determining the content of mercury in the sample S quantitatively through processing of signals fed from the detector.

Figure 2:
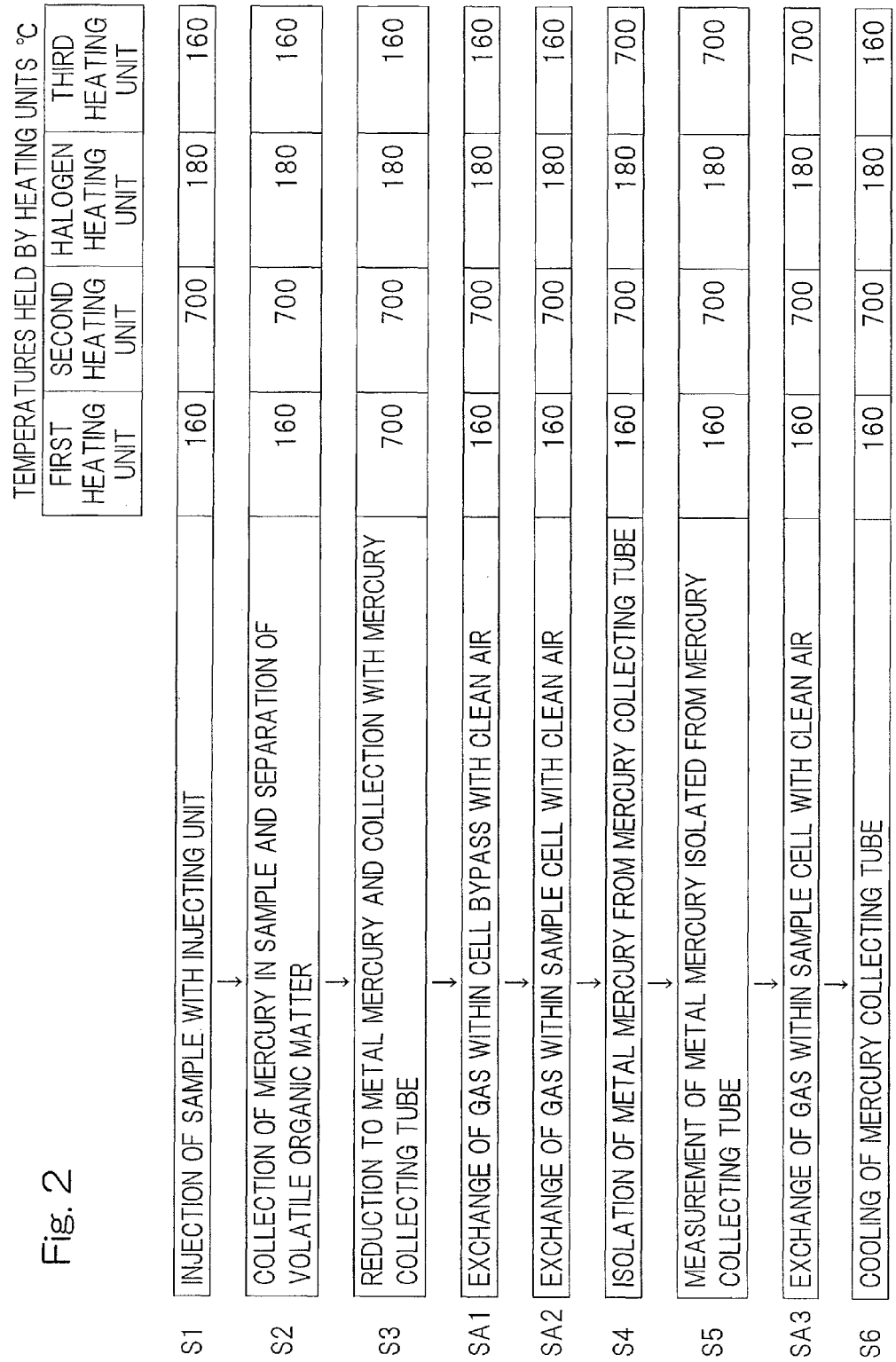
FIG. 2 illustrates a flow chart showing the sequence of operation of the mercury measuring apparatus.

Respective operations of the mercury measuring apparatus 100 at process steps and associated heating temperatures (° C.) to which heating is made by the corresponding heating units are shown in FIG. 2. Under the control of the control unit 4, the mercury measuring apparatus 100 executes in sequence, a sample injecting step S1 of injecting the sample S into the injector 3; a collecting and separating step S2 of causing mercury, contained in the sample S, to be collected by the first adsorbent 11 and then separating and discharging a volatile organic matter; a mercury reducing and collecting step S3 of heating and vaporizing mercury, collected by the first adsorbent 11, to the first heating unit 12, reducing monovalent and bivalent mercury into metal mercury with the reducing agent 13 heated by the second heating unit 14, and causing the metal mercury to be collected in the mercury collecting tube 18 filled with the second adsorbent 17; after the reduction and collection of the mercury, a gas exchange step SA1 of exchanging a gas within a cell bypass 53 bypassing the sample cell 21, with a clean air; after the exchange of the gas within the cell bypass 53, a gas exchange step SA2 of exchanging a gas within the mercury collecting tube 18 and the sample cell 21 with a clean air; a metal mercury isolating step S4 of isolating the metal mercury from the second adsorbent 17 by heating the mercury collecting tube 18 by means of the third heating unit 19; a measuring step S5 of causing the mercury measuring unit 2 to measure the metal mercury isolated from the mercury collecting tube 18; after the measurement, a gas exchange step SA3 of exchanging a gas within the mercury collecting tube 18 and the sample cell 21 with a clean air; and a cooling step S6 of cooling the mercury collecting tube 18. Depending on the foregoing process steps described above, the flow switching valves V1, V2, V3, V5 and V6 are selectively controlled to establish respective gas passages FP1, FP2, FP31 and FP4 for each of those process steps.

In the case of the measurement that does not require a high precision, the gas exchange steps SA1, SA2 and SA3 may be dispensed with.

Figure 3:
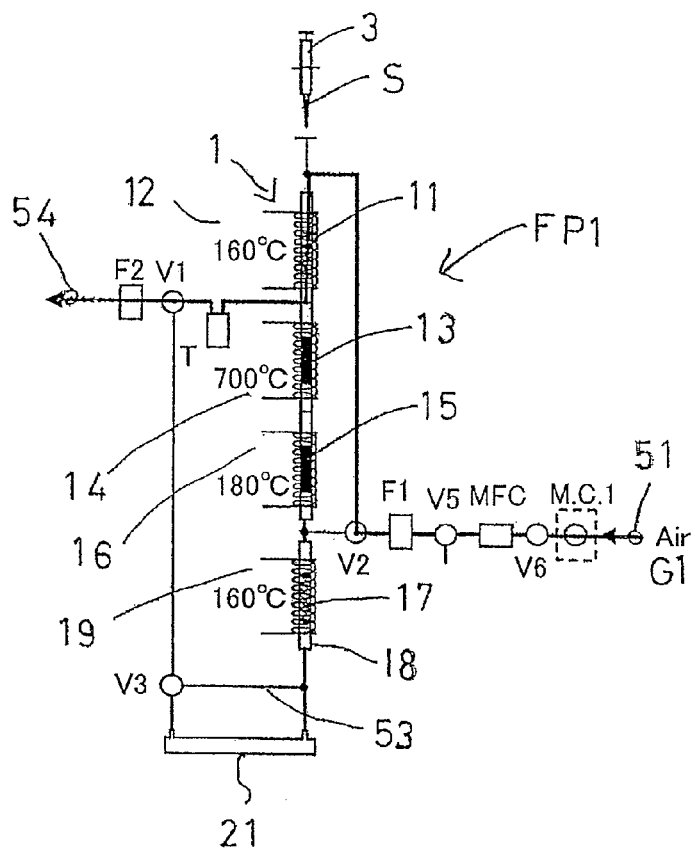
FIG. 3 illustrates an explanatory diagram showing how an injection of a sample and a collecting and separating step are performed in the mercury measuring apparatus.

Since the gas passages FP1, FP2, FP3 and FP4 are selectively defined depending on the process steps performed by the mercury measuring apparatus 100, those will now be described in detail. During the sample injecting step S1 and the collecting and separating step S2, as best shown in FIG. 3, the injecting and collecting passage FP1 is established, in which an air G1 flows sequentially through a gas introducing port 51 to which the gas G1 is introduced from an air compressor; a mist catcher MC1 for removing moisture and/or oil components contained in the air G1; the flow switching valve V6; a mass-flow controller MFC for adjusting the flow of the air G1; the flow switching valve V5; a mercury removal filter F1 filled with a filler material for removal of mercury contained in the air G1 as an impurity; the flow switching valve V2; the adsorbent 11 filled in the column 1; a gas-liquid separating tube T; the flow switching valve V1; a mercury removal filter F2; and a gas discharge port 54.

Figure 4:
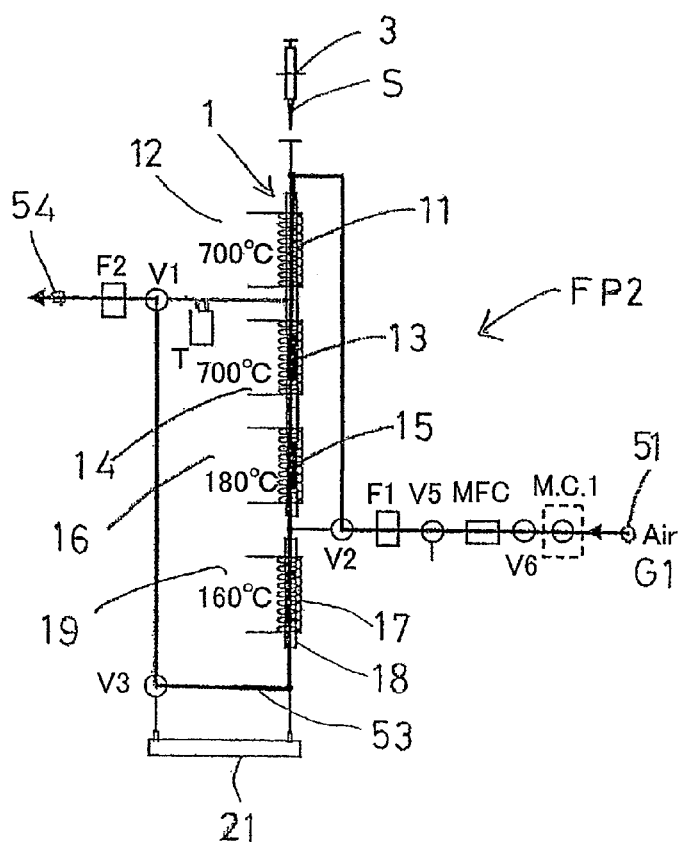
FIG. 4 illustrates an explanatory diagram showing how a mercury reducing and collecting step is performed in the mercury measuring apparatus.

During the mercury reducing and collecting step S3, as best shown in FIG. 4, the reducing and collecting passage FP2 is established, in which a carrier gas G1 flows sequentially through the gas introducing port 51; the mist catcher MC1; the flow switching valve V6; the mass-flow controller MFC; the flow switching valve V5; the mercury removal filter F1; the flow switching valve V2; the adsorbent 11 filled in the column 1; the reducing agent 13 filled in the column 1; the acidic substance removing agent 15 filled in the column 1; the mercury collecting tube 18; the cell bypass 53; the flow switching valve V3; the flow switching valve V1; the mercury removal filter F2; and the gas discharge port 54.

Figure 5:
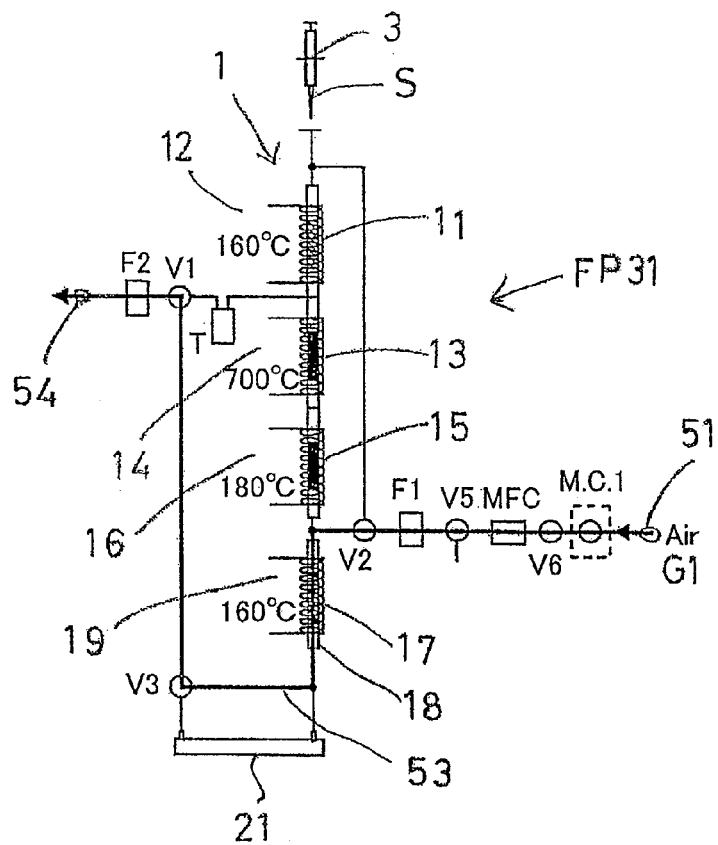
FIG. 5 illustrates an explanatory diagram showing how a first step for gas exchanging is performed in the mercury measuring apparatus.

During the gas exchange step SA1, as best shown in FIG. 5, the gas exchange passage FP31 is established, in which the air G1 flows sequentially through the gas introducing port 51; the mist catcher MC1; the flow switching valve V6; the mass-flow controller MFC; the flow switching valve V5; the mercury removal filter F1; the flow switching valve V2; the mercury collecting tube 18; the cell bypass 53; the flow switching valve V3; the flow switching valve V1; the mercury removal filter F2; and the gas discharge port 54.

Figure 6:
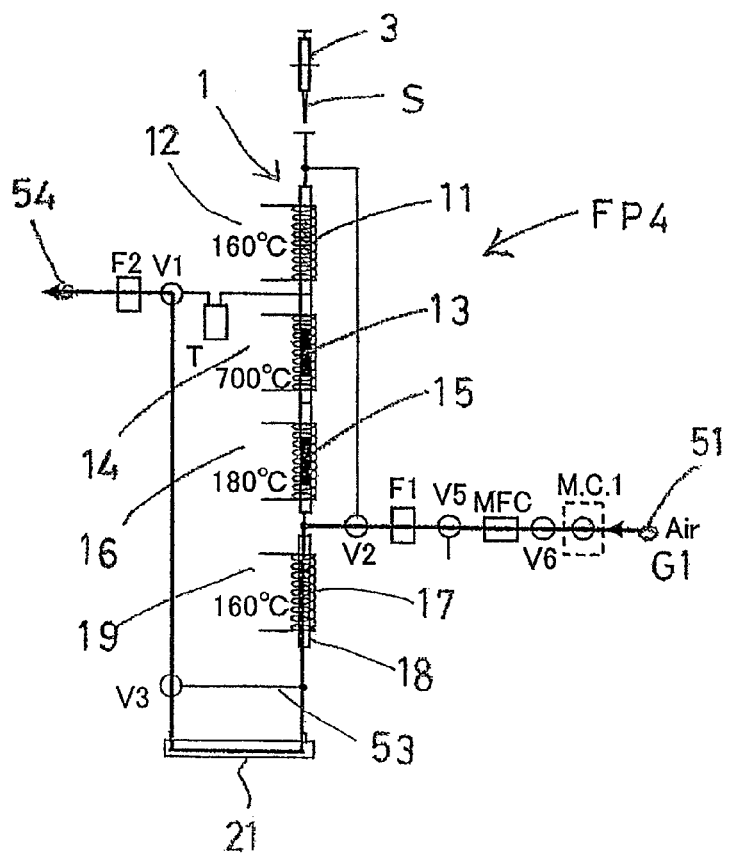
FIG. 6 illustrates an explanatory diagram showing how a second step for gas exchanging is performed in the mercury measuring apparatus.

During the gas exchange step SA2, as best shown in FIG. 6, the measuring passage FP4 is established, in which the air G1 flows sequentially through the gas introducing port 51; the mist catcher MC1; the flow switching valve V6; the mass-flow controller MFC; the flow switching valve V5; the mercury removal filter F1; the flow switching valve V2; the mercury collecting tube 18; the sample call 21; the flow switching valve V3; the flow switching valve V1; the mercury removal filter F2; and the gas discharge port 54.

Figure 7:
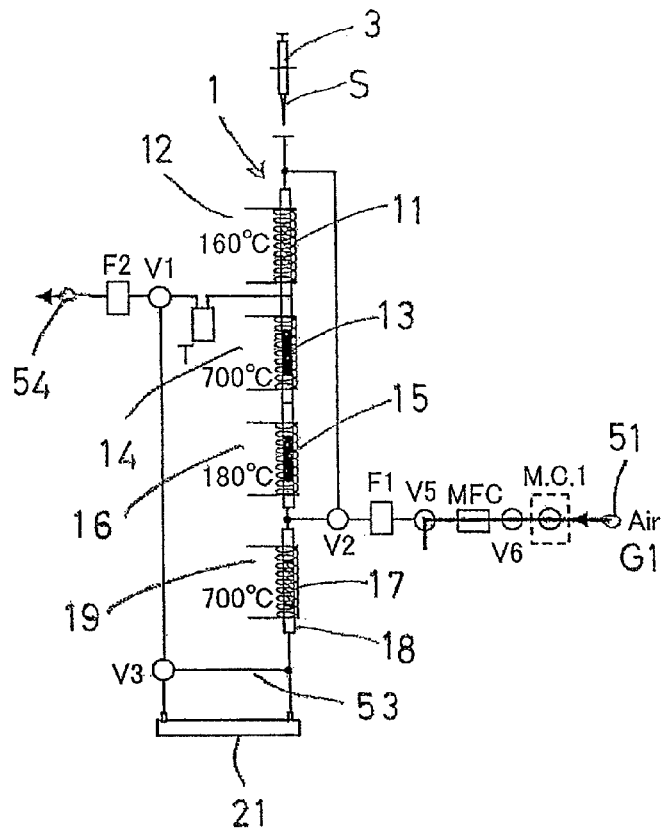
FIG. 7 illustrates an explanatory diagram showing how a metal mercury isolating step is performed in the mercury measuring apparatus.

During the metal mercury isolating step S4, as best shown in FIG. 7, the air G1 flows sequentially through the gas introducing port 51; the mist catcher MC1; the flow switching valve V6; the mass-flow controller MFC; and the flow switching valve V5 and is then discharged from the flow switching valve V5 to the outside of the mercury measuring apparatus 100.

Figure 8:
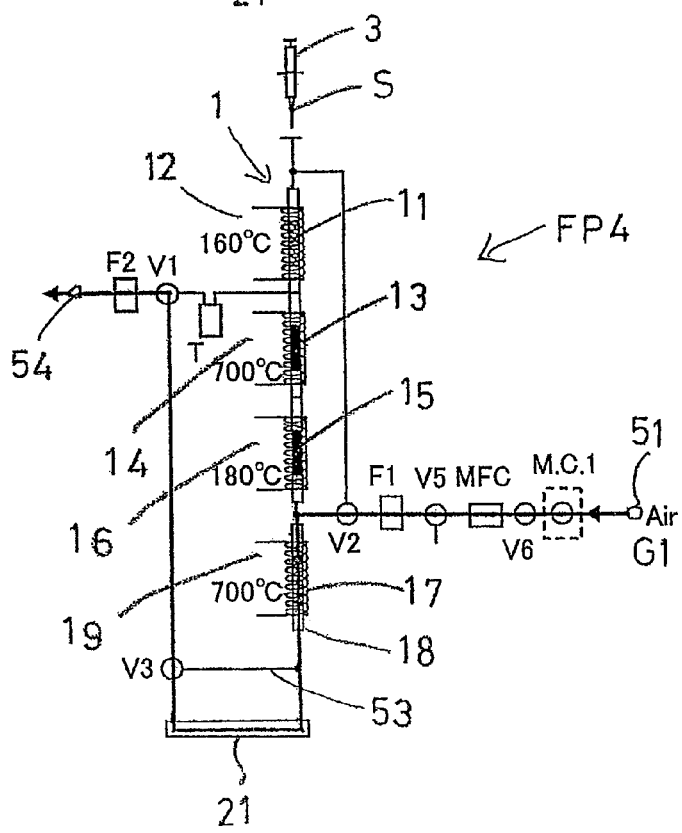
FIG. 8 illustrates an explanatory diagram showing how a third step for gas exchanging step and a measuring step are performed in the mercury measuring apparatus.

During the measuring step and the gas exchange step SA3, as best shown in FIG. 8, the gas exchange passage FP4 is established, in which the air G1 flows sequentially through the gas introducing port 51; the mist catcher MC1; the flow switching valve V6; the mass-flow controller MFC; the flow switching valve V5; the mercury removal filter F1; the flow switching valve V2; the mercury collecting tube 18; the sample cell 21; the flow switching valve V3; the flow switching valve V1; the mercury removal filter F2 and the gas discharge port 54.

Figure 9:
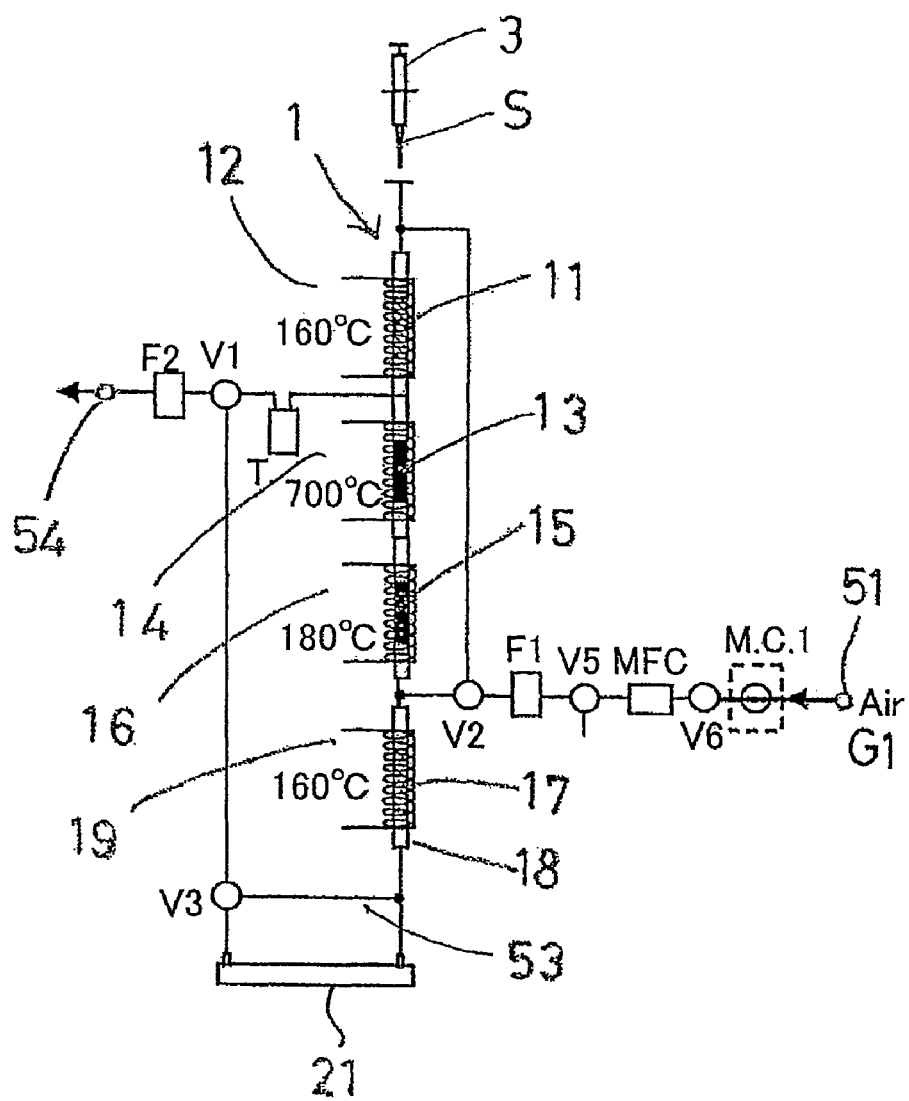
FIG. 9 illustrates an explanatory diagram showing how a cooling step is performed in the mercury measuring apparatus.

During the cooling step S6, as best shown in FIG. 9, the flow switching valve V6 is closed and, therefore, no air G1 flows inside the mercury measuring apparatus 100.

For the first adsorbent to be filled in the column 1, an adsorbent such as, for example, activated alumina ($Al_2O_3$), gold coated chromosorb or beach sands coated with gold, which has an excellent capability of adsorbing particularly organic mercury (a mercury compound such as, for example, dimethyl mercury), which is harmful during the manufacture of petrochemical products, and also adsorbing metal mercury can be advantageously employed.

In particular, the former, i.e., the activated alumina has an excellent capability of adsorbing organic mercury whereas the latter materials have an excellent capability of adsorbing metal mercury. With respect to the injector 3, a microsyringe can be suitably employed and the use of it makes it possible to inject the sample S into the column 1 all at once in a matter of minutes.

For the reducing agent 13 filled to be filled in the column 1, reducing agents such as, for example, copper oxide and manganese sesquioxide are employed and arranged in series with each other within the column 1. For the second adsorbent 17 to be filled in the mercury collecting tube 18, an adsorbent such as, for example, gold coated chromosorb is employed. The acidic substance removing agent 15 is employed to adsorb and remove acidic substances mixed in the sample, which composes mainly of hydrocarbon, and the air G1 (the carrier gas) and sodium carbonate, for example, is employed therefor. Each of the mercury removal filters F1 and F2 is filled with a filler material such as, for example, activated carbon for exclusive use with mercury, which is effective to remove mercury mixed in the air G1 (the carrier gas). Accordingly, a measurement error, which would be brought about by the air G1 (the carrier gas) during the mercury measurement, can be avoided.

The first heating unit 12, the second heating unit 14, the third heating unit 19 and the acidic substance removing agent heating unit 16 are in the form of heating wires spirally wound around the column 1 and outer tubular walls of the mercury collecting tube 18, respectively, and are controlled by the control unit 4 to perform heating of those components to respective temperatures for respective lengths of time that are appropriate to the respective process step including the collecting and separating step and the mercury reducing and collecting step. The mercury measuring unit 2 may be either a mercury atomic absorption spectrophotometer or a mercury atomic fluorescence spectrophotometer. Each of the flow switching valves V1, V2, V3 and V5 used to form the gas passages that are selectively established according to the collecting and separating step and the mercury reducing and collecting step is employed in the form of a three-way switching valve whereas the flow switching valve V6 is employed in the form of a two-way switching valve, and, in any event, those flow switching valves are controlled by the control unit 4 so as to establish the passages discussed hereinabove.

Hereinafter, the operation of the mercury measuring apparatus 100 will be described in detail. This mercury measuring apparatus 100 is controlled by the control unit 4 so as to operate according to the flowchart shown in FIG. 2 under conditions set up by the control unit 4. Prior to the operation of the mercury measuring apparatus 100, the air G1, which is a carrier gas, is supplied by and from the air compressor (not shown) to the gas introducing port 51. When the mercury measuring apparatus 100 is electrically powered on, the first heating unit 12 is maintained at 160° C., the second heating unit 14 is maintained at 700° C., the acidic substance removing agent heating unit 16 is maintained at 180° C., and the third heating unit 19 is maintained at 160° C.

As shown in FIG. 3, during the sample injecting step S1, the flow switching valve V6 is first opened and the flow switching valves V1, V2, V3 and V5 are switched to establish the flow in predetermined directions, respectively, to thereby define the injecting and collecting passage FP1. By the mass-flow controller MFC controlled by the control unit 4, the flow of the air G1 supplied from the gas introducing port 51 is adjusted to about 0.2 L/min. As the air G1 flows through the mercury removal filter F1, mercury mixed in the air G1 is adsorbed and removed by the activated carbon for exclusive use with mercury, which is filled inside the mercury removal filter F1, and the air G1, from which the mercury has been removed, is then supplied to the first adsorbent 11.

Also, in a condition in which the air G1 flows through the column 1, a sample S to be measured, which contains hydrocarbon such as, for example, naphtha as a principal component, is injected into the inside of the column by the injector 3. Each of the heating units are maintained at the respective temperature, which is the same as that when the apparatus has been electrically powered on.

As shown in FIG. 3, during the collecting and separating step S2, the injecting and collecting passage FP1, which is the same as that during the sample injecting step S1, is defined and, since the first adsorbent 11 is heated to 160° C., metal mercury contained in the sample S that has been injected by the injector 3 is gasified to flow through the activated alumina and is then adsorbed by the gold coated chromosorb, and organic mercury contained in the sample is adsorbed by the activated alumina. When the sample S flows through the first adsorbent 11 together with the air G1, the organic mercury and the metal mercury both mixed in the sample S are adsorbed by the first adsorbent 11 and separated from volatile organic matter. The sample S, from which the mercury has been removed, is discharged through the gas discharge port 54 to the outside of the mercury measuring apparatus 100 together with the air G1, followed by removal from the first adsorbent 11.

As shown in FIG. 4, during the mercury reducing and collecting step S3, the reducing and collecting passage FP2 is defined. By heating the organic mercury and the metal mercury, both collected by the first adsorbent 11 in the column 1, with the first heating unit 12 to 700° C., those mercury are vaporized from the first adsorbent 11. Monovalent and divalent mercury vaporized from the organic mercury is reduced into metal mercury in the presence of the reducing agent 13, which is positioned at a location downstream of the first adsorbent 11 and is then heated by the second heating unit 14 to 700° C. The metal mercury so reduced and the metal mercury isolated from the first adsorbent 11 are transported by the air G1 to the acidic substance removing agent 15, which is positioned at a location downstream of the reducing agent 13 and is then heated by the acidic substance removing agent heating unit 16 to 180° C., followed by removal of an acidic substance mixed in the air G1 and an acidic substance generated during the heating and vaporization. Thereafter, the metal mercury reduced in the manner described above and the metal mercury isolated from the first adsorbent 11 are collected in the mercury collecting tube 18 then filled with the second adsorbent 17.

As shown in FIG. 5, during the gas exchange step SA1, the gas exchange passage FP31 is defined and a gaseous medium flowing in the gas exchange passage FP31 including the cell bypass 53 bypassing the sample cell 21 is exchanged with a clean air G1.

As shown in FIG. 6, during the gas exchange step SA2, the measuring passage FP4 is defined and a gaseous medium flowing in the gas exchange passage FP4 including the sample cell 21 is exchanged with a clean air G1.

As shown in FIG. 7, during the metal mercury isolating step S4, the mercury collecting tube 18 is heated by the third heating unit 19 to 700° C. and the metal mercury is isolated from the second adsorbent 17. At this time, the air G1 flows to the outside of the mercury measuring apparatus 100 through the flow switching valve V5 and, hence, no air G1 flows in the mercury collecting tube 18, but the metal mercury isolated from the second adsorbent 17 remains accumulated in the vicinity of the inside of the mercury collecting tube 18. As shown in FIG. 8, during the measuring step S5, the measuring passage FP4 is defined and the metal mercury isolated from the mercury collecting tube 18 then heated by the third heating unit to 700° C. is transported by the air G1 to the sample cell 21 of the mercury atomic absorption spectrometer 2, which is a mercury measuring unit, and is then measured.

As shown in FIG. 8, during the gas exchange step SA3, the gas exchange passage FP32 is defined and a gaseous medium flowing in the measuring passage FP4 including the mercury collecting tube 18, then heated by the third heating unit 19 to 700° C., and the sample cell 21 is exchanged with a clean air G1.

As shown in FIG. 9, during the cooling step S6, the flow switching valve V6 is closed and, hence, no air G1 flows inside the mercury measuring apparatus 100. The holding temperature of the third heating unit 19 is lowered from 700° C. down to 160° C. and the mercury collecting tube 18 is cooled. If the next succeeding sample is desired to be measured thereafter, the turntable of the sample exchanger 6 is turned to place the next succeeding sample immediately below the injector 3 so that the sample injecting step S1 can be repeated.

With the mercury measuring apparatus 100 according to the first preferred embodiment of the present invention, since the process ranging from collection of the sample containing mainly of hydrocarbon to measurement is performed automatically, the operator need not insert the column, in which the mercury has been adsorbed, in the mercury measuring unit such as required according to the system disclosed in the Patent Document 1 referred to previously. Also, since the mercury measuring apparatus 100 is of the closed system, high precision data can be obtained and the apparatus can be easily handled to accomplish the intended measurement in a matter of minutes. Also, since during the sample injecting step, the collecting and separating step, the mercury reducing and collecting step, the metal mercury isolating step and the measuring step, the first adsorbent 11, the reducing agent 13, the acidic substance removing agent 15 and the second adsorbent 17 are heated by the first heating unit, the second heating unit, the acidic substance removing agent heating unit and the third heating unit to the respective optimum temperatures necessary for them to work sufficiently and the mercury mixed in the sample composed mainly of hydrocarbon can be assuredly separated and collected and isolated, it is possible to achieve a highly precise measurement.

Figure 10:
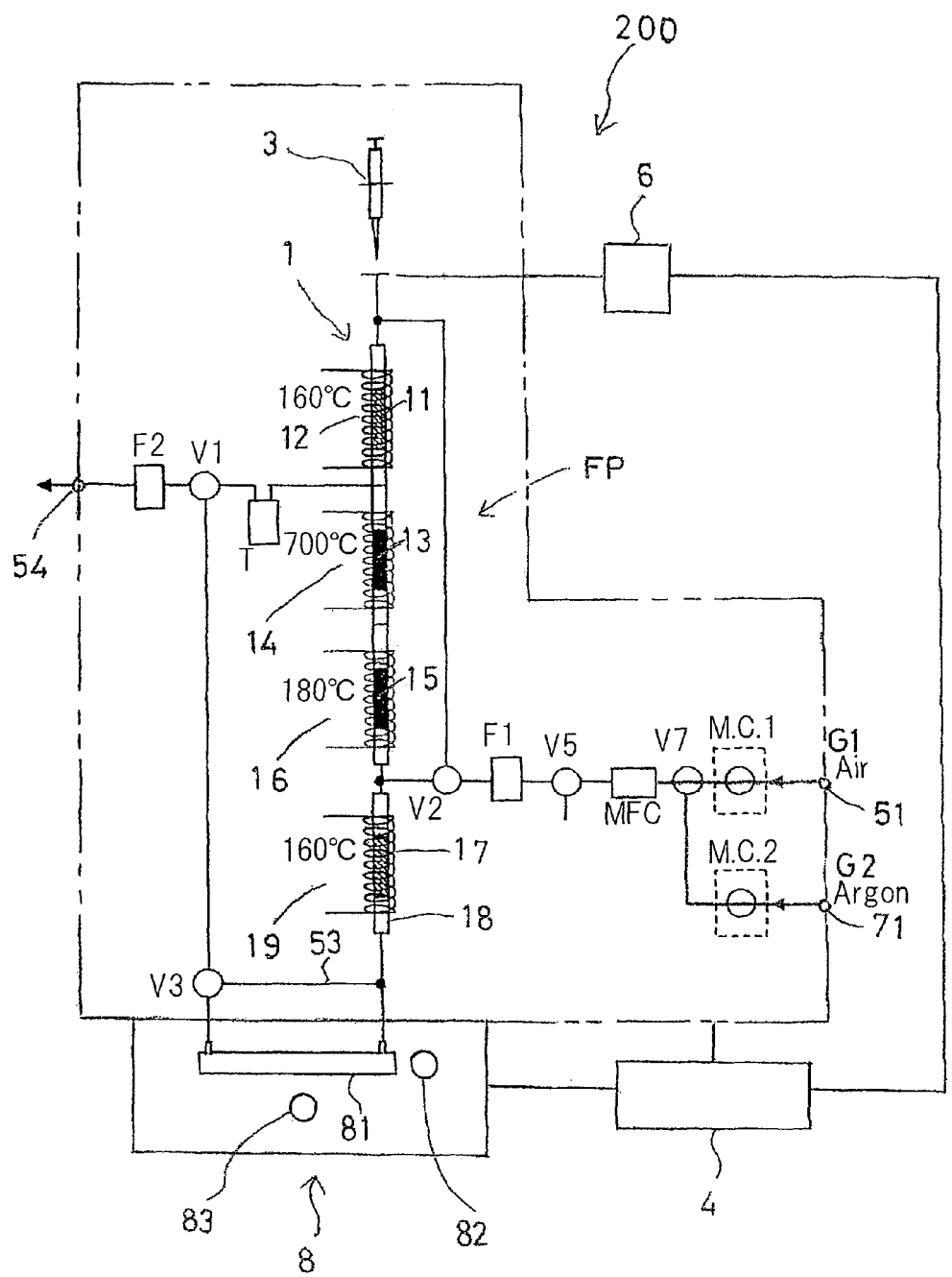
FIG. 10 illustrates a schematic block diagram showing the mercury measuring apparatus according to a second preferred embodiment of the present invention.

A mercury measuring apparatus according to a second preferred embodiment of the present invention is schematically shown in FIG. 10 and is now identified by 200. It is to be noted that an air G1 as a first carrier gas, fed from an air compressor (not shown), for example, which is provided outside the mercury measuring apparatus 200, is supplied to the gas introducing port 51 of the mercury measuring apparatus 200 and an argon (Ar) gas G2 as a second carrier gas fed from an argon (Ar) gas container (not shown) is supplied to a gas introducing port 71 of the measuring apparatus 200. This mercury measuring apparatus 200 is substantially similar to the mercury measuring apparatus 100, but differs therefrom in that the mercury measuring apparatus 200 is provided with the second gas introducing port 71, to which the argon gas G2 is supplied as the second carrier gas and that the mercury measuring unit is employed in the form of a mercury atomic fluorescence spectrophotometer 8. In this mercury measuring apparatus 200, in order to switch the air G1, used as the first carrier gas, over to the argon gas G2, used as the second carrier gas, at a predetermined process step, a flow switching valve V7, which is a three-way switching valve, is employed in place of the flow switching valve V6. It is also to be noted that in place of the air G1, an oxygen gas may be employed as the first carrier gas and that the column 1 or a column separate from the column 1 may be provided with a sulfur removing agent for removing a sulfur component contained in the sample.

The mercury measuring unit includes a mercury lamp 82 for emitting an analytical line of 253.7 nm of mercury, a sample cell 81 for introducing metal mercury which has been collected and isolated, and a detector 83 for detecting fluorescence of the mercury generated from the sample within the sample cell 81 that has been radiated with the analytical line of the mercury lamp 82 and is employed in the form of a mercury atomic fluorescence spectrophotometer 8 capable of determining the content of mercury in the sample through processing of signals fed from the detector.

As shown in the flowchart in FIG. 11, the mercury measuring apparatus 200 executes sequentially the sample injecting step S1, the collecting and separating step S2, the mercury reducing and collecting step S3, the gas exchange step SB1, the gas exchange step SB2, a gas exchange step SB3, a gas exchange step SB4, the metal mercury isolating step S4, the measuring step S5, a gas exchange step SB5 and the cooling step S6, and during a process from the sample injecting step S1 to the mercury reducing and collecting step S3, the air G1 is supplied as the first carrier gas whereas during a process from the gas exchange step SB 1 to the measuring step S5, the argon gas G2 is supplied as the second carrier gas.

Figure 12:
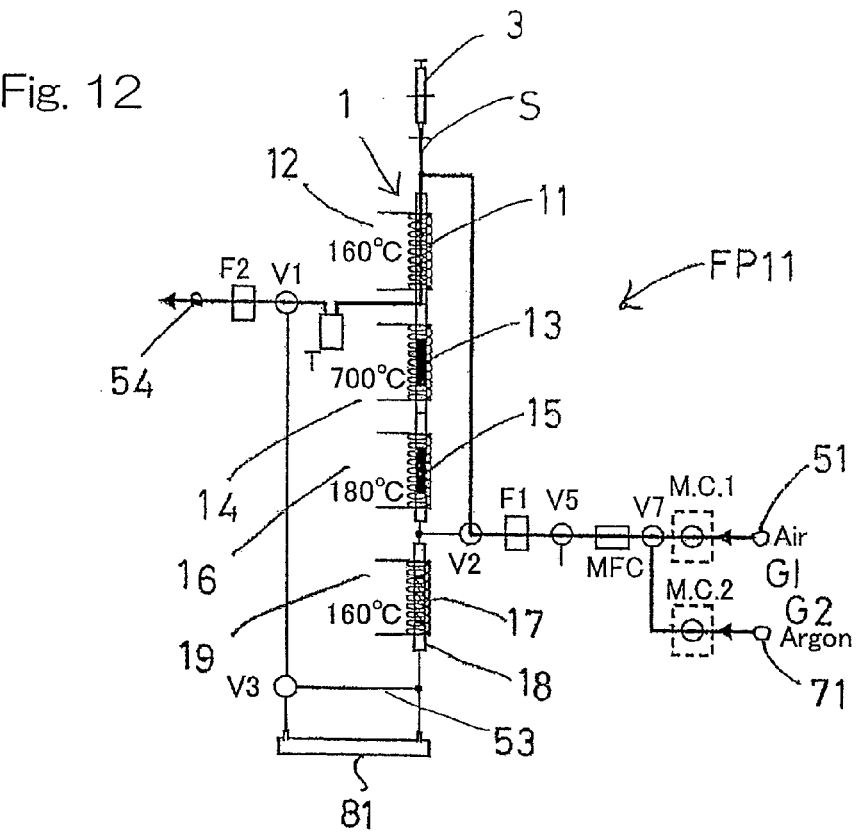
FIG. 12 illustrates an explanatory diagram showing how the injection of the sample and the collecting and separating step are performed in the mercury measuring apparatus according to the second embodiment.

During the sample injecting step S1 and the collecting and separating step S2, as shown in FIG. 12, an injecting and collecting passage FP11 is defined, along which the air G1 flows sequentially through the gas introducing port 51 for introducing the air G1 as the first carrier gas, the mist catcher MC1 for removing moisture and/or oil components mixed in the air G1, the flow switching valve V7, the mass-flow controller MFC for adjusting the flow of the air G1 or the argon gas G2 used as the second carrier gas, the flow switching valve V5, the mercury removing filter F1 filled with the filler material and capable of removing mercury mixed in the air G1 or the argon gas G2, the flow switching valve V2, the first adsorbent 11, the gas-liquid separating tube T, the flow switching valve V1, the mercury removing filter F2 and the gas discharge port 54.

Figure 13:
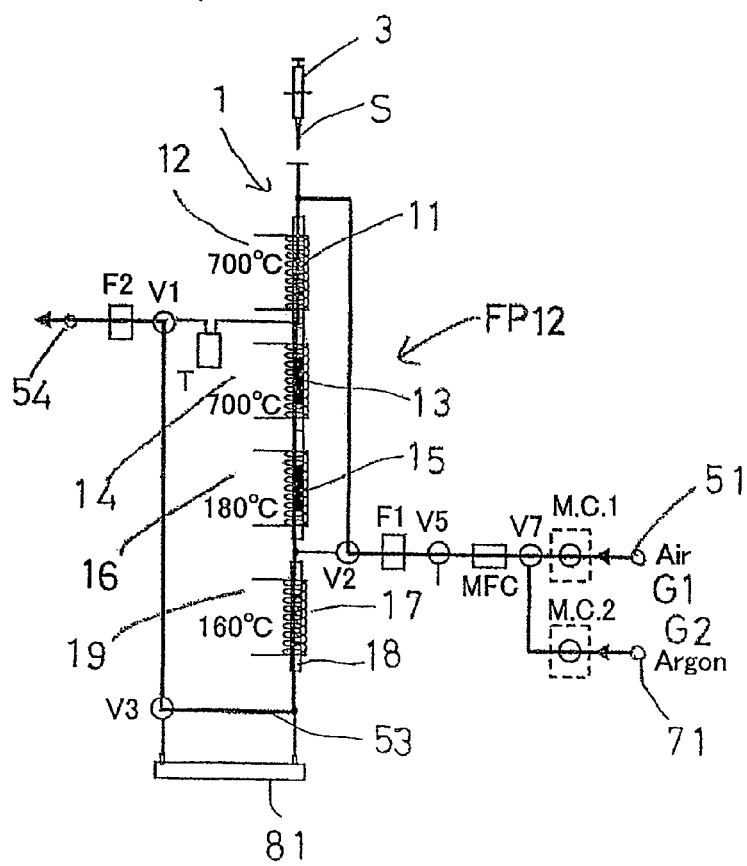
FIG. 13 illustrates an explanatory diagram showing how the mercury reducing and collecting step is performed in the mercury measuring apparatus according to the second embodiment.

During the mercury reducing and collecting step S3, as shown in FIG. 13, a reducing and collecting passage FP12 is defined, along which the air G1 flows sequentially through the gas introducing port 51, the mist catcher MC1, the flow switching valve V7, the mass-flow controller MFC, the flow switching valve V5, the mercury removing filter F1, the flow switching valve V2, the first adsorbent 11, the reducing agent 13, the acidic substance removing agent 15, the mercury collecting tube 18, the cell bypass 53, the flow switching valve V3, the flow switching valve V1, the mercury removing filter F2 and the gas discharge port 54.

Figure 14:
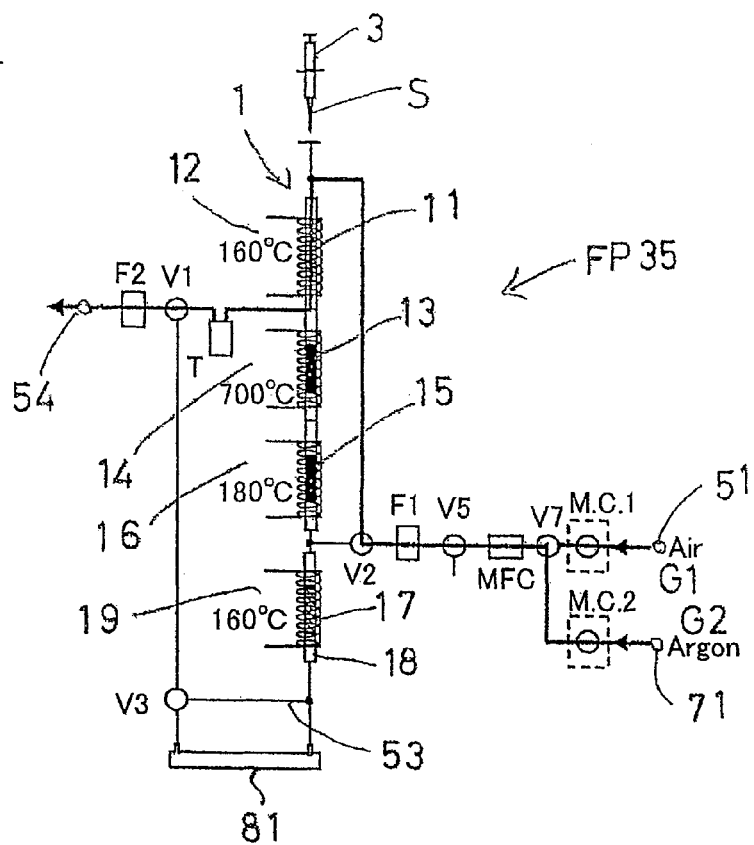
FIG. 14 illustrates an explanatory diagram showing how the first step for gas exchanging is performed in the mercury measuring apparatus according to the second embodiment.

During the gas exchange step SB1, as shown in FIG. 14, a gas exchange FP35 is defined, along which the argon gas G2 flows sequentially through the gas introducing port 71 to which the argon gas G2 used as the second carrier gas is introduced, a mist catcher MC2 for removing moisture and/or oil components contained in the argon gas G2, the flow switching valve V7, the mass-flow controller MFC, the flow switching valve V5, the mercury removing filter F1, the flow switching valve V2, the first adsorbent 11, the gas-liquid separating tube T, the flow switching valve V1, the mercury removing filter F2 and the gas discharge port 54.

Figure 15:
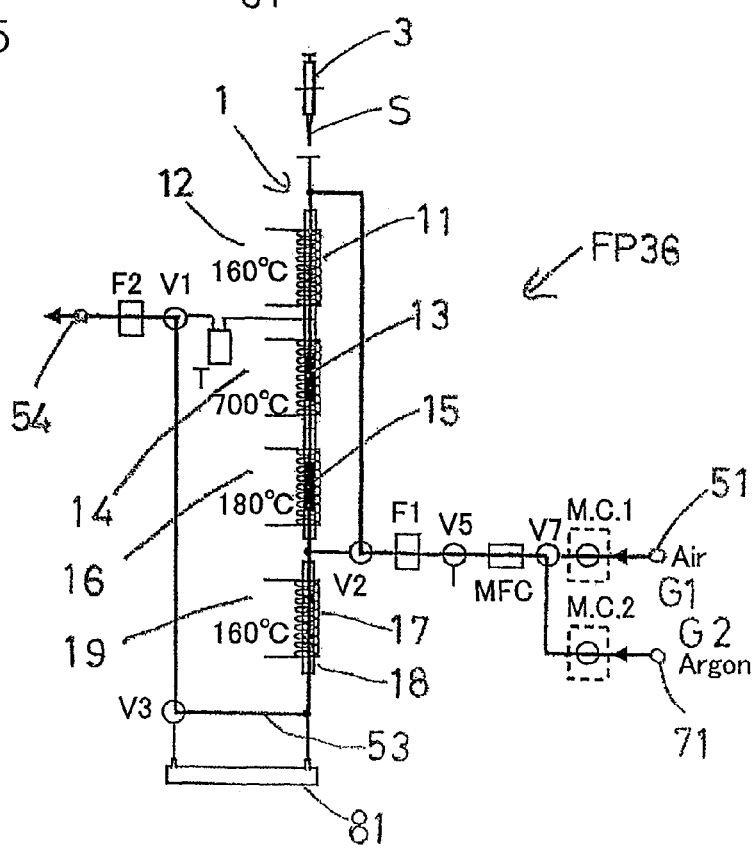
FIG. 15 illustrates an explanatory diagram showing how the second step for gas exchanging is performed in the mercury measuring apparatus according to the second embodiment.

During the gas exchange step SB2, as shown in FIG. 15, a gas exchange passage FP36 is defined, along which the argon gas G2 flows sequentially through the gas introducing port 71, the mist catcher MC2, the flow switching valve V7, the mass-flow controller MFC, the flow switching valve V5, the mercury removing filter F1, the flow switching valve V2, the first adsorbent 11, the reducing agent 13, the acidic substance removing agent 15, the mercury collecting tube 18, the cell bypass 53, the flow switching valve V3, the flow switching valve V1, the mercury removing filter F2 and the gas discharge port 54.

Figure 16:
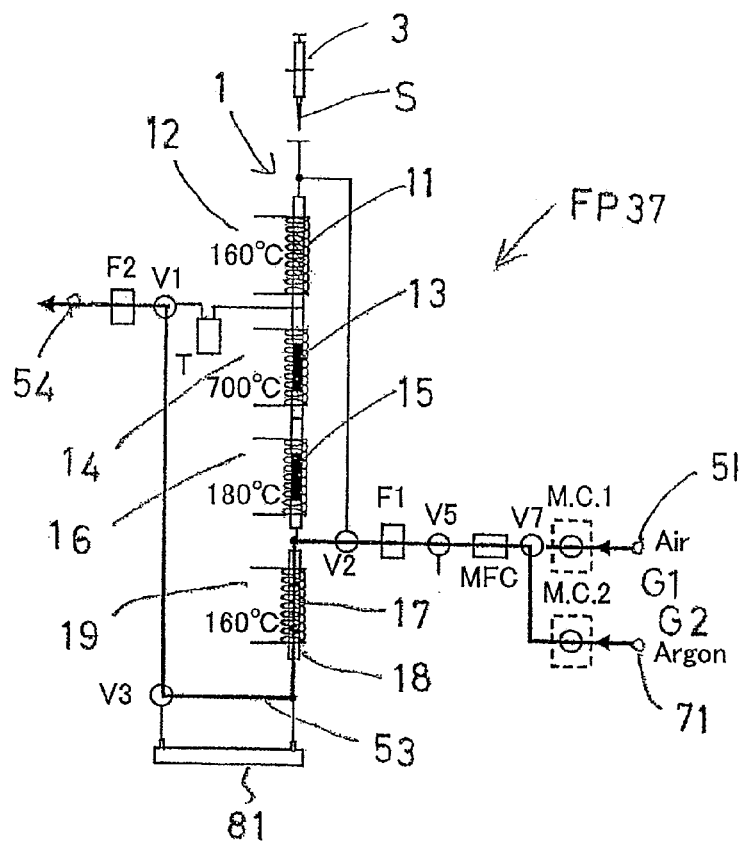
FIG. 16 illustrates an explanatory diagram showing how a third step for gas exchanging is performed in the mercury measuring apparatus according to the second embodiment.

During the gas exchange step SB3, as shown in FIG. 16, a gas exchange passage FP37 is defined, along which the argon gas G2 flows sequentially through the gas introducing port 71, the mist catcher MC2, the flow switching valve V7, the mass-flow controller MFC, the flow switching valve V5, the mercury removing filter F1, the flow switching valve V2, the mercury collecting tube 18, the cell bypass 53, the flow switching valve V3, the flow switching valve V1, the mercury removing filter F2 and the gad discharge port 54.

Figure 17:
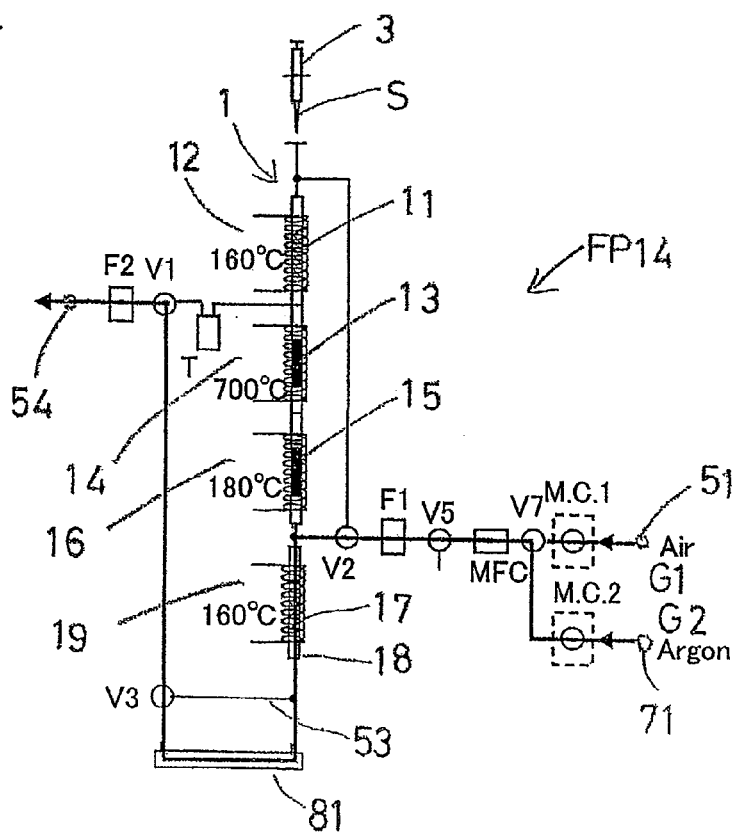
FIG. 17 illustrates an explanatory diagram showing how a fourth step for gas exchanging is performed in the mercury measuring apparatus according to the second embodiment.

During the gas exchange step SB4 and the measuring step S5, as shown in FIG. 17, a measuring passage FP14 is defined, along which the argon gas G2 flows sequentially along the gas introducing port 71, the mist catcher MC2, the flow switching valve V7, the mass-flow controller MFC, the flow switching valve V5, the mercury removing filter F1, the flow switching valve V2, the mercury collecting tube 18, the sample cell 81, the flow switching valve V3, the flow switching valve V1, the mercury removing filter F2 and the gas discharge port 54.

Figure 18:
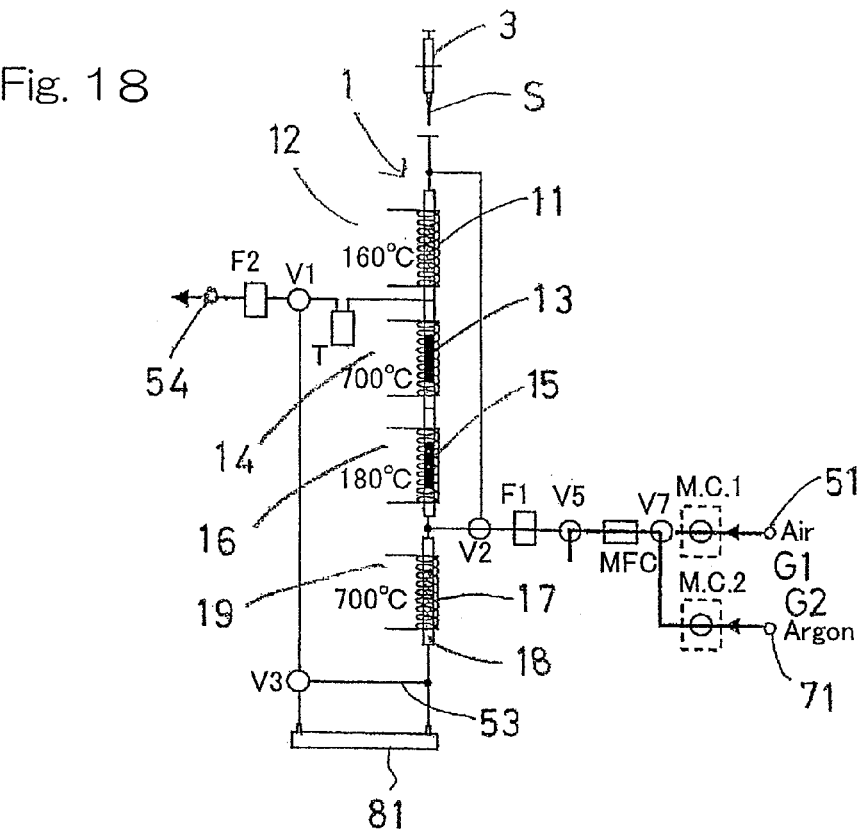
FIG. 18 illustrates an explanatory diagram showing how the metal mercury isolating step is performed in the mercury measuring apparatus according to the second embodiment.

During the metal mercury isolating step S4, as shown in FIG. 18, the argon gas G2 flows sequentially through the gas introducing port 71, the mist catcher MC2, the flow switching valve V7, the mass-flow controller MFC and the flow switching valve V5, followed by discharge thereof through the flow switching valve V5 to the outside of the mercury measuring apparatus 200.

Figure 19:
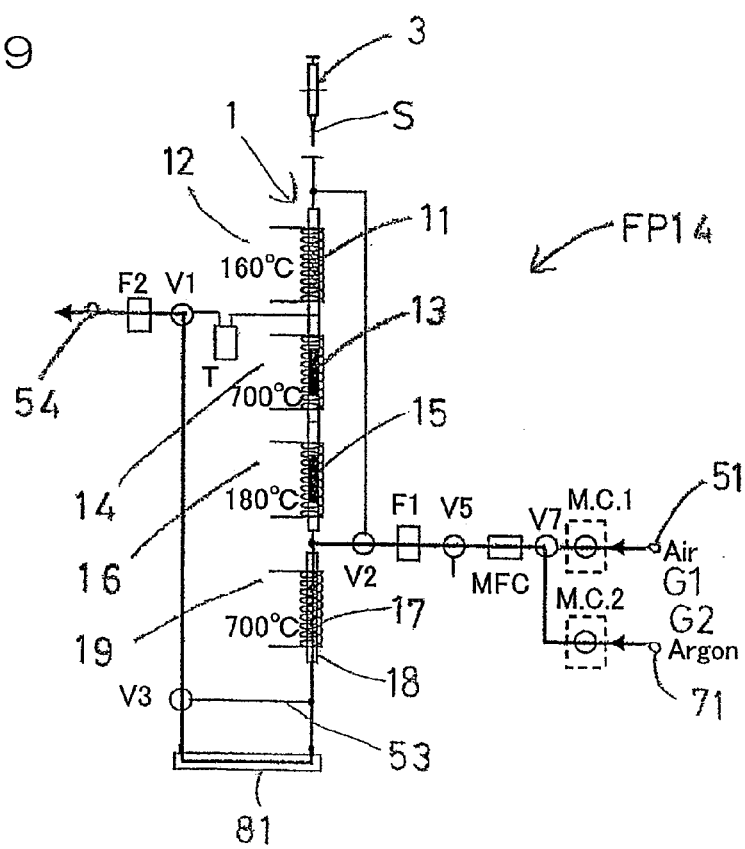
FIG. 19 illustrates an explanatory diagram showing how a measuring step is performed in the mercury measuring apparatus according to the second embodiment.

During the measuring step S5, as shown in FIG. 19, a measuring passage FP14 is defined, along which the argon gas G2 flows sequentially through the gas introducing port 71, the mist catcher MC2, the flow switching valve V7, the mass-flow controller MFC, the flow switching valve V5, the mercury removing filter F1, the flow switching valve V2, the mercury collecting tube 18, the sample call 81, the flow switching valve V3, the flow switching valve V1, the mercury removing filter F2 and the gas discharge port 54.

Figure 20:
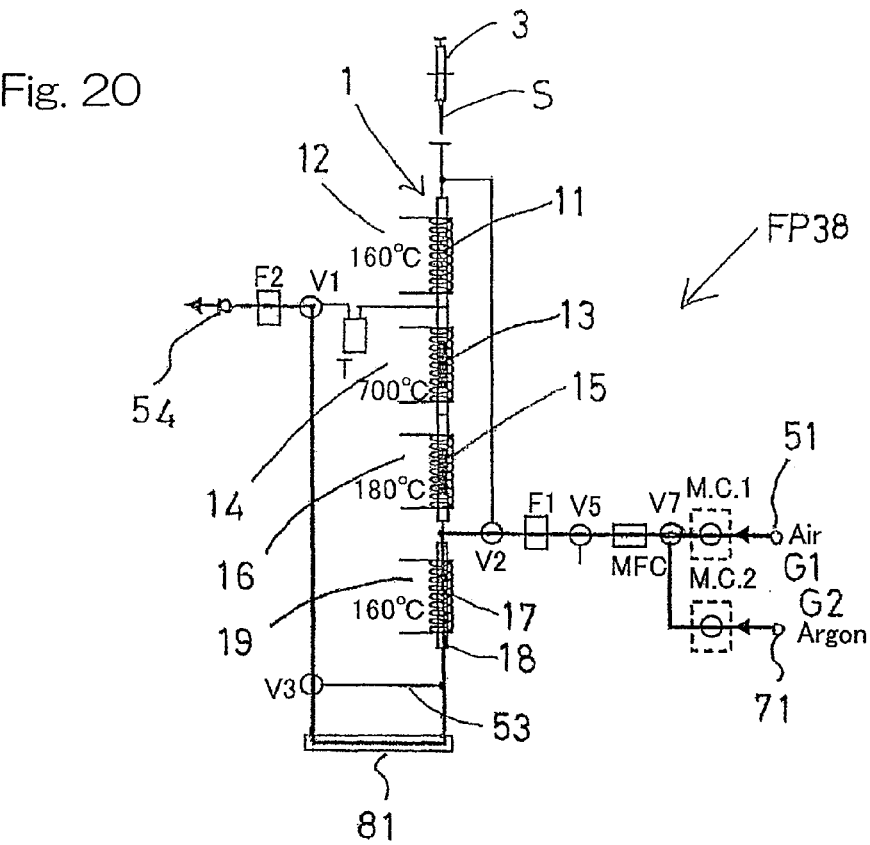
FIG. 20 illustrates an explanatory diagram showing how a fifth step for gas exchanging is performed in the mercury measuring apparatus according to the second embodiment.

During the gas exchange step SB5, as shown in FIG. 20, a measuring passage FP38 is defined, along which the air G1 flows sequentially through the gas introducing port 51, the mist catcher MC1, the flow switching valve V7, the mass-flow controller MFC, the flow switching valve V5, the mercury removing filter F1, the flow switching valve V2, the mercury collecting tube 18, the sample cell 81, the flow switching valve V3, the flow switching valve V1, the mercury removing filter F2 and the gas discharge port 54.

Figure 21:
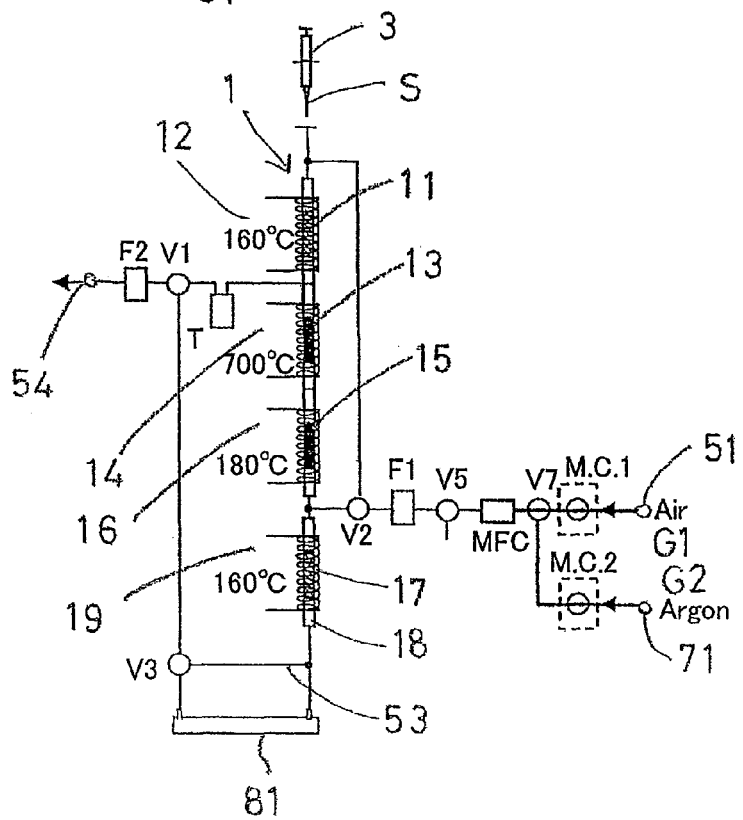
FIG. 21 illustrates an explanatory diagram showing how the cooling step is performed in the mercury measuring apparatus according to the second embodiment.

During the cooling step S6, as shown in FIG. 21, the flow switching valve V7 is closed and, hence, neither the air G1 nor the argon gas G2 flow inside the mercury measuring apparatus 200.

In the next place, the operation of the mercury measuring apparatus 200 will be described with particular reference to the flowchart shown in FIG. 11. Prior to the operation of the mercury measuring apparatus 200, the air G1 is supplied to the gas introducing port 51 and the argon gas G2 is also supplied to the gas introducing port 71. When the mercury measuring apparatus 20 is electrically powered on, the first heating unit is held at 160° C., the second heating unit is held at 700° C., the acidic substance removing agent heating unit is held at 180° C., and the third heating unit is held at 160° C.

During the sample injecting step S1 shown in FIG. 12, the injecting and collecting passage FP11 is first established. By the mass-flow controller MFC then controlled by the control unit 4, the flow of the air G1 supplied from the gas introducing port 51 is adjusted to about 0.2 L/min.

Also, in a condition in which the air G1 flows through the column 1, a sample S to be measured such as, for example, naphtha is injected thereinto through the injector 3. The heating units are maintained at the respective temperature, which is the same as that when the apparatus has been electrically powered on.

During the collecting and separating step S2 shown in FIG. 12, the same collecting injecting and collecting passage FP11 as that during the sample injecting step S1 is defined and the first adsorbent 11 is heated to 160° C., and, therefore, metal mercury contained in the sample S that has been injected by the injector 3 is gasified to flow through the activated alumina and is then adsorbed by the gold coated chromosorb and organic mercury contained in the sample is adsorbed by the activated alumina. When the sample S flows through the first adsorbent 11 together with the air G1, the organic mercury and the metal mercury both mixed in the sample S are adsorbed by the first adsorbent 11 and separated from volatile organic matter. The sample S, from which the mercury has been removed, is discharged through the gas discharge port 54 to the outside of the mercury measuring apparatus 200 together with the air G1, followed by removal from the first adsorbent 11.

As shown in FIG. 13, during the mercury reducing and collecting step S3, a reducing and collecting passage FP12 is defined. By heating the organic mercury and the metal mercury, both collected by the first adsorbent 11 in the column 1, with the first heating unit 12 to 700° C., those mercury are vaporized from the first adsorbent 11. Monovalent and divalent mercury vaporized from the organic mercury is reduced into metal mercury in the presence of the reducing agent 13, which is positioned at a location downstream of the first adsorbent 11 and is then heated by the second heating unit 14 to 700° C. The metal mercury so reduced and the metal mercury isolated from the first adsorbent 11 are subsequently transported by the air G1 to the acidic substance removing agent 15, which is positioned at a location downstream of the reducing agent 13 and is then heated by the acidic substance removing agent heating unit 16 to 180° C., followed by removal of an acidic substance mixed in the air G1 and an acidic substance generated during the heating and vaporization. Thereafter, the metal mercury reduced in the manner described above and the metal mercury isolated from the first adsorbent 11 are collected in the mercury collecting tube 18 then filled with the second adsorbent 17.

As shown in FIG. 14, during the gas exchange step SB1, a gas exchange passage FP35 is defined. A clean argon gas G2 flows through a portion of the column 1, in which the first adsorbent 11 has been filled, and a gaseous medium within the gas exchange passage FP35, including the first adsorbent 11, is exchanged with the clean argon gas G2.

As shown in FIG. 15, during the gas exchange step SB2, the gas exchange passage FP36 is established. A clean argon gas G2 flows through the column 1 and the mercury collecting tube 18 and a gaseous medium within the gas exchange passage FP36, including the column 1 and the mercury collecting tube 18, is exchanged with the clean argon gas G2.

As shown in FIG. 16, during the gas exchange step SB3, a gas exchange passage FP37 is defined and a gaseous medium within the gas exchange passage FP37, including the cell bypass 53, is exchanged with the clean argon gas G2.

As shown in FIG. 17, during the gas exchange step SB4, a measuring passage FP14 is defined and a gaseous medium within the gas exchange passage FP14, including the sample cell 81, is exchanged with the clean argon gas G2.

As shown in FIG. 18, during the metal mercury isolating step S4, a mercury collecting tube 18 is heated by the third heating unit 19 to 700° C. and the metal mercury is isolated from the second adsorbent 17. At this time, the argon gas G2 flows from the flow switching valve V5 to the outside of the mercury measuring apparatus 200 and, hence, no argon gas G2 flow through the mercury collecting tube 18, but the metal mercury isolated from the second adsorbent 17 remain accumulated in the vicinity of the inside of the mercury collecting tube 18.

During the measuring step S5 shown in FIG. 19, a measuring passage FP14 is defined and the metal mercury isolated from the mercury collecting tube 18 then heated by the third heating unit 19 to 700° C. is transported by the argon gas G2 to the sample cell 81 and measured by the mercury atomic fluorescence spectrophotometer 8, which is the mercury measuring unit.

As shown in FIG. 20, during the gas exchange step SB5, a gas exchange passage FP38 is defined and the gaseous medium within the gas exchange passage FP38, including the mercury collecting tube 18, then heated by the third heating unit 19 to 700° C., and the sample cell 81, is exchanged with a clean air G1. It is to be noted that the process may proceed directly from the measuring step S5 to the cooling step S6 without the gas exchange step SB5 intervening therebetween.

During the cooling step S6 shown in FIG. 21, the flow switching valve V7 is closed and, hence, no air G1 nor argon gas G2 flow through the inside of the mercury measuring apparatus 200. The third heating unit 19 is lowered from 700° C. down to 160° C. and the mercury collecting tube 18 is cooled accordingly. Thereafter, where the next succeeding sample is to be measured, the turntable of the sample exchange 6 is turned to allow the next succeeding sample to be moved to a position below the injector 3, with the sample injecting step S1 repeated accordingly.

With the mercury measuring apparatus 200 according to the second preferred embodiment of the present invention, since the process ranging from collection of the sample, containing mainly of hydrocarbon, to measurement is performed automatically, the operator need not insert the column, in which the mercury has been adsorbed, in the mercury measuring unit such as required according to the system disclosed in the Patent Document 1 referred to previously. Also, since the mercury measuring apparatus 200 is of the closed system, high precision data can be obtained and the apparatus can be easily handled to accomplish the intended measurement in a matter of minutes. Also, since during the sample injecting step, the collecting and separating step, the mercury reducing and collecting step, the metal mercury isolating step and the measuring step, the first adsorbent 11, the reducing agent 13, the acidic substance removing agent 15 and the second adsorbent 17 are heated by the first heating unit, the second heating unit, the acidic substance removing agent heating unit and the third heating unit to the respective optimum temperatures necessary for them to work sufficiently and the mercury mixed in the sample containing mainly of hydrocarbon can be assuredly separated and collected and isolated, it is possible to achieve a highly precise measurement. Also, since during the collecting and separating step and the mercury reducing and collecting step the air G1 is caused to flow, those reactions can be facilitated, and when the argon gas G2 is caused to flow from the metal mercury isolating step and the measuring step, a highly sensitive measurement can be accomplished with the mercury atomic fluorescence spectrophotometer 8.

Although in the practice of each of the first and second preferred embodiments of the present invention, the metal mercury isolating step S4 has been shown and described as followed by the measuring step S5, the metal mercury isolating step S4 and the measuring step S5 may be performed simultaneously. In such case, in the case of the first preferred embodiment, the measuring passage FP1 shown in FIG. 8 is defined and the metal mercury is, while being isolated from the second adsorbent 17, transported by the air G1 to and measured by the mercury atomic absorption spectrophotometer 2, which is the mercury measuring unit. On the other hand, in the case of the second preferred embodiment, the measuring passage FP14 shown in FIG. 19 is defined and the mercury collecting tube 18 is heated by the third heating unit 19 to 700° C. and the metal mercury is, while being isolated from the second adsorbent 17, transported by the argon gas G2 to the sample cell 81 of the mercury atomic fluorescence spectrophotometer 8, which is the mercury measuring unit, and then measured by the mercury atomic fluorescence spectrophotometer 8. If the metal mercury isolating step S4 and the measuring step S5 are performed simultaneously, and if the sample S contains a large amount of mercury, the measuring sensitivity can be lowered and the measurement can be accomplished without the sample S being diluted with a solvent.

Also, although in the practice of any one of the first and second preferred embodiments of the present invention, the mercury adsorbent has been shown and described as employed in the form of the activated alumina and the gold coated chromosorb, any other known adsorbent may be employed. The reducing agent has been shown and described as employed in the form of manganese sesquioxide and copper oxide, any other known reducing agents may be employed. In addition, although the use of the sample exchanger 6 has been shown and described in the foregoing description, mercury mixed in, for example, LPG (liquefied petroleum gas) can be measured if any known mercury collecting tube burning unit is employed.

Although the present invention has been fully described in connection with the preferred embodiments thereof with reference to the accompanying drawings which are used only for the purpose of illustration, those skilled in the art will readily conceive numerous changes and modifications within the framework of obviousness upon the reading of the specification herein presented of the present invention. Accordingly, such changes and modifications are, unless they depart from the scope of the present invention as delivered from the claims annexed hereto, to be construed as included therein.

What is claimed is:

1. A mercury measuring apparatus for measuring mercury contained in a sample composed mainly of hydrocarbon, which apparatus comprises:
   a column accommodating therein a first adsorbent for adsorbing mercury and a reducing agent for reducing monovalent and bivalent mercury into a metal mercury;
   an injector for injecting the sample into the column;
   a first heating unit for heating the first adsorbent within the column;
   a second heating unit for heating the reducing agent within the column;
   a mercury collecting tube filled with a second adsorbent for adsorbing the metal mercury;
   a third heating unit for heating the mercury collecting tube;
   a mercury measuring unit for measuring by introducing the metal mercury, which is isolated from the mercury collecting tube then heated by the third heating unit, into a sample cell;
   a gas flow path defining one of an injecting and collecting passage for introducing a carrier gas from a gas introducing port so as to flow through the first adsorbent and discharging the carrier gas from a gas discharge port, a reducing and collecting passage for introducing the carrier gas from the gas introducing port so as to flow through the first adsorbent, a reducing agent and a second adsorbent and discharging the carrier gas from the gas discharge port, and a measuring passage for introducing the carrier gas from the gas introducing port so as to flow through the second adsorbent and a sample cell and discharging the carrier gas from the gas discharge port;
   a flow path switching valve for selecting one of the gas flow passages; and
   a control unit for controlling the first heating unit, the second heating unit, the third heating unit, the injector, the flow path switching valve and the mercury measuring unit.

2. The mercury measuring apparatus as claimed in claim 1, in which the control unit executes:
   a sample injecting step of injecting a sample into the injector;
   a collecting and separating step of collecting mercury, contained in the sample, to the first adsorbent and subsequently separating and discharging a volatile organic matter;

a mercury reducing and collecting step of causing the first heating unit to heat and vaporize mercury, collected by the first adsorbent, reducing monovalent and bivalent mercury into metal mercury by causing the second heating unit to heat the reducing agent, and causing the metal mercury to be collected by the mercury collecting tube filled with the second adsorbent;

a metal mercury isolating step of causing the third heating unit to heat the mercury collecting tube to isolate the metal mercury from the second adsorbent; and a measuring step of measuring the metal mercury, which has been isolated from the mercury collecting tube, with the mercury measuring unit.

3. The mercury measuring apparatus as claimed in claim 2, in which the control unit executes the metal mercury isolating step and the measuring step simultaneously.

4. The mercury measuring apparatus as claimed in claim 1, in which the gas flow path comprises a first gas introducing port, through which a first carrier gas is introduced, and a second gas introducing port, through which a second carrier gas is introduced, and the mercury measuring unit is a mercury atomic fluorescence spectrophotometer.

5. The mercury measuring apparatus as claimed in claim 4, in which the first carrier gas is introduced from the first gas introducing port during the sample injecting step, the collecting and separating step and the mercury reducing and collecting step, but the second carrier gas is introduced from the second gas introducing port during the metal mercury isolating step and the measuring step and in which the mercury measuring unit is a mercury atomic fluorescence spectrophotometer.

6. The mercury measuring apparatus as claimed in claim 1, further comprising a sample exchanger for exchanging a plurality of samples and the control unit controls the sample exchanger.

* * * * *